United States Patent [19]

Martel et al.

[11] Patent Number: 4,665,169

[45] Date of Patent: May 12, 1987

[54] CARBAPENEM ANTIBIOTICS

[75] Inventors: Alain Martel, Delson; Carol Bachand, Candiac, both of Canada

[73] Assignee: Bristol-Myers Company, New York, N.Y.

[21] Appl. No.: 774,628

[22] Filed: Sep. 11, 1985

[51] Int. Cl.$^4$ .................... C07D 487/04; A61K 31/40
[52] U.S. Cl. .................................................. 540/350
[58] Field of Search ................ 260/245.2 T; 540/310, 540/350; 514/210

[56] References Cited

U.S. PATENT DOCUMENTS

| | | | |
|---|---|---|---|
| 3,950,357 | 4/1976 | Kahan et al. | 424/274 |
| 4,232,036 | 11/1980 | Christensen et al. | 424/274 |
| 4,235,920 | 11/1980 | Christensen et al. | 424/274 |
| 4,309,346 | 1/1982 | Christensen et al. | 260/239 |
| 4,536,335 | 8/1987 | Kim et al. | 260/245.2 T |

FOREIGN PATENT DOCUMENTS

| | | |
|---|---|---|
| 0001627 | 5/1979 | European Pat. Off. . |
| 0001628 | 5/1979 | European Pat. Off. . |
| 0010317 | 4/1980 | European Pat. Off. . |
| 0017992 | 10/1980 | European Pat. Off. . |
| 0021082 | 1/1981 | European Pat. Off. . |
| 0037080 | 10/1981 | European Pat. Off. . |
| 0037081 | 10/1981 | European Pat. Off. . |
| 0037082 | 10/1981 | European Pat. Off. . |
| 0038869 | 11/1981 | European Pat. Off. . |
| 0040408 | 11/1981 | European Pat. Off. . |
| 2118183 | 10/1983 | United Kingdom . |
| 2119371 | 11/1983 | United Kingdom . |
| 2122196 | 1/1984 | United Kingdom . |
| 2128187 | 4/1984 | United Kingdom . |

OTHER PUBLICATIONS

Recent Advances in Chemistry of β-Lactam Antibiotices, Royal Society of Chemistry, London, 1981, pp. 240–254.

Primary Examiner—Nicholas S. Rizzo
Attorney, Agent, or Firm—David M. Morse

[57] ABSTRACT

Novel carbapenem antibiotics are prepared in which the 2-substituent has the formula

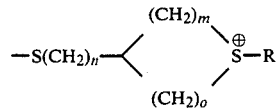

wherein n is 0, 1, 2, 3, m, is 1 or 2, and R is $C_1$–$C_6$ alkyl, allyl, propargyl, carboxymethyl, cyanomethyl or aralkyl wherein the aryl moiety is phenyl or heteroaryl and the alkyl moiety is $C_1$–$C_6$ alkyl, said heterocyclic ring containing the sulfonium group being optionally substituted at a ring carbon atom or atoms by one or two $C_1$–$C_6$ alkyl groups.

14 Claims, No Drawings

CARBAPENEM ANTIBIOTICS

BACKGROUND OF THE INVENTION

1. Field of the Invention

The present invention is directed to new carbapenem antibiotics in which the 2-substituent has the formula

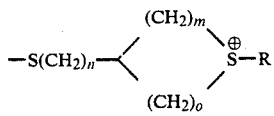

wherein n is 0, 1, 2, or 3, m is 1 or 2, o is 1 or 2, and R is $C_1$–$C_6$ alkyl, allyl, propargyl, carboxymethyl, cyanomethyl or aralkyl where the aryl moiety is phenyl or heteroaryl and the alkyl moiety is $C_1$–$C_6$ alkyl, said heterocyclic ring containing the sulfonium group being optionally substituted at a ring carbon atom or atoms by one or two $C_1$–$C_6$ alkyl groups.

2. Description of the Prior Art

A number of β-lactam derivatives containing the carbapenem nucleus

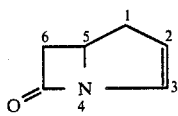

have been disclosed in the literature. These carbapenem derivatives have been reported to possess utility as antibacterial agents and or β-lactamase inhibitors.

The initial carbapenem compounds were natural products such as thienamycin of the formula

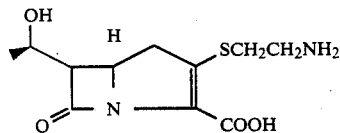

obtained by fermentation of *Streptomyces cattleya* (U.S. Pat. No. 3,950,357). Thienamycin is an exceptionally potent broad-spectrum antibiotic which possesses notable activity against various Pseudomonas species, organisms which have been notoriously resistant to β-lactam antibiotics.

Compounds of the formula

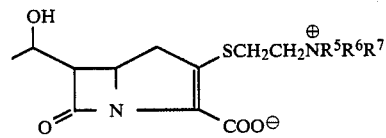

wherein $R^5$, $R^6$ and $R^7$ are independently selected from H and substituted or unsubstituted: alkyl, alkenyl, alkynyl, cycloalkyl, cycloalkenyl, cycloalkenylalkyl, cycloalkylalkyl, aryl, aralkyl, heteroaryl or heteroaralkyl are disclosed in U.S. Pat. No. 4,235,920. Among the compounds disclosed in U.S. Pat. No. 4,235,920 is

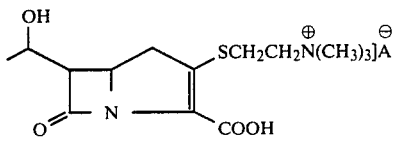

wherein A is a pharmaceutical acceptable anion. The abovementioned quaternary amine derivative is also described in *Recent Advances in Chemistry of β-Lactam Antibiotics*, Royal Society of Chemistry, London, 1981, pg 240–254, where its antibacterial activity on average is reported as approximately ½ to ⅔ that of thienamycin.

Compounds of the formula

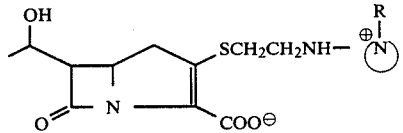

wherein

attached to the amino nitrogen group of thienamycin represents a mono- or polycyclic N-containing heterocyclic group and R is H, substituted or unsubstituted: alkyl, aryl, alkenyl, heterocyclyalkenyl, aralkenyl, heterocyclyalkyl, aralkyl, —$NR_2$, COOR, $CONR_2$, —OR, or CN, are disclosed in European patent application No. 21082.

European Patent Application No. 40,408 discloses compounds of the formula

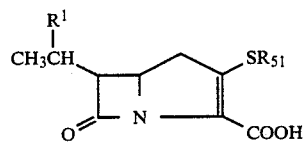

wherein $R^1$ is H, methyl or hydroxyl and $R_{51}$ is a monovalent organic group including inter alia heterocyclicalkyl.

European Patent Application No. 38,869 discloses compounds of the formula

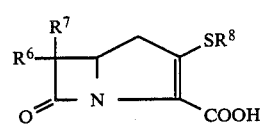

wherein $R^6$, $R^7$, and $R^8$ are independently selected from the group consisting of hydrogen, substituted and unsubstituted: alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; aryl, such as phenyl; aralkyl, aralkenyl, and aralkynyl wherein the aryl moiety is phenyl and the aliphatic portion has 1–6 carbon atoms; heteroaryl, heteroaralkyl, heterocyclyl and heterocyclylalkyl; wherein the substituent or substituents relative to the above-named radicals are selected from the group consisting of:

—X° halo (chloro, bromo, fluoro)
—OH hydroxy
—OR¹ alkoxy, aryloxy

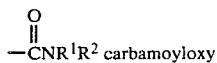 —CNR¹R² carbamoyloxy

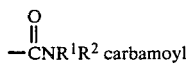 —CNR¹R² carbamoyl

—NR¹R² amino

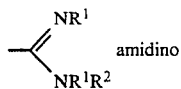 amidino

R¹
—NO₂ nitro

—N(R¹)₃⁺ tri-substituted amino (R¹ group independently chosen)

R¹
—C=NOR² oximino
—SR¹ alkyl- and arylthio
—SO₂NR¹R² sulfonamido

 —NHCNR¹R² ureido

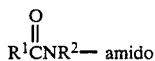 R¹CNR²— amido

—CO₂H carboxy
—CO₂R¹ carboxylate

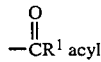 —CR¹ acyl

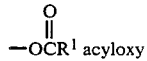 —OCR¹ acyloxy

—SH mercapto

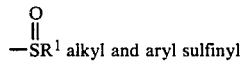 —SR¹ alkyl and aryl sulfinyl

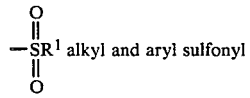 —SR¹ alkyl and aryl sulfonyl

—CN cyano
—N₃ azido wherein, relative to the above listed substituents on R⁶, R⁷, and R⁸, the groups R¹ and R² are independently selected from: hydrogen, alkyl, alkenyl, and alkynyl, having from 1–10 carbon atoms; cycloalkyl, cycloalkylalkyl, and alkylcycloalkyl, having 3–6 carbon atoms in the cycloalkyl ring and 1–6 carbon atoms in the alkyl moieties; aryl, such as phenyl; aralkyl, aralkenyl, and aralkynyl wherein the aryl moiety is phenyl and the aliphatic portion has 1–6 carbon atoms; heteroaryl, heteroaralkyl, heterocyclyl and heterocyclylalkyl and wherein the hetero atom or atoms in the above-named heterocyclic moieties are selected from the group consisting of 1–4 oxygen, nitrogen or sulphur atoms and wherein the alkyl moieties associated with said heterocyclic moieties have 1–6 carbon atoms. (See also European Patent Applications Nos. 1627, 1628, 10317, 17992, 37080, 37081 and 37082).

At the Gordon Research Conference on Medicinal Chemistry held at New London, N.H. on Aug. 2–6, 1982, a handout was distributed in which a variety of carbapenem antibiotics were disclosed. Among the compounds disclosed on page 9 of the handout is the carbapenem of the formula

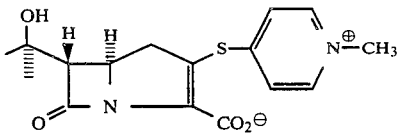

The above-mentioned carbapenem derivative is also disclosed on page 145 of European Patent Applicaton No. 38869 and on page 252 of European Patent Application No. 17992.

U.S. Pat. No. 4,309,346 discloses carbapenum derivatives having 2-substituents of the formula

—SR⁸ where R⁸ may be inter alia heteroaralkyl in which the hetero atom or atoms in heteroaralkyl may be selected from the group consisting of 1–4 oxygen, nitrogen or sulfur atoms. No disclosure is made of any sulfonium groups such as are present in the compounds of the present invention.

European Patent Application No. 10,317 (see also U.S. Pat. No. 4,232,036) discloses carbapenem compounds of the general formula

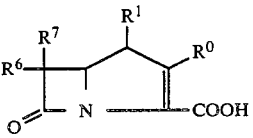

where R⁰ is H or —SR⁸; R¹, R⁶, R⁷ and R⁸ are independently selected from the group consisting of hydrogen (R¹ is not H), substituted and unsubstituted: alkyl, alkenyl and alkynyl, having from 1–10 carbon atoms; cycloalkyl, cycloalkylalkyl and alkylcycloalkyl, having 3–6 carbon atoms in the cycloalkyl ring and 1–6 carbon atoms in the alkyl moieties; phenyl; aralkyl, aralkenyl, and aralkynyl wherein the aryl moiety is phenyl and the alkyl chain has 1–6 carbon atoms; heteroaryl, heteroaralkyl, heterocyclyl and heterocyclylalkyl wherein the substituent or substituents relative to the above-named radicals are selected from the group consisting of: amino, mono-, di-, and trialkylamino, hydroxyl, alkoxyl, mercapto, alkylthio, phenylthio, sulfamoyl, amidino, guanidino, nitro, chloro, bromo, fluoro, cyano and carboxy; and wherein the hetero atom or atoms in the above-named heterocyclic moieties are selected from the group consisting of 1–4 oxygen, nitrogen or sulfur atoms; and wherein the alkyl moieties of the above-recited substituents have 1–6 carbon atoms.

U.K. Patent Application No. 2,119,371A discloses carbapenem antibiotics characterized by a 2-substituent of the formula

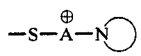

in which A represents cyclopentylene, cyclohexylene or $C_2$–$C_6$ alkylene optionally substituted by one or more $C_1$–$C_4$ alkyl groups and

represents a quaternized nitrogen-containing aromatic heterocycle.

U.K. Patent Application No. 2,122,196A discloses carbapenem antibiotics characterized by a 2-substituent of the formula

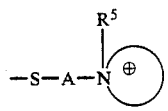

in which A represents cyclopentylene, cyclohexylene or $C_2$–$C_6$ alkylene optionally substituted by one or more $C_1$–$C_4$ alkyl groups; $R^5$ represents either (a) an optionally substituted aliphatic, cycloaliphatic, cycloaliphatic-aliphatic, aryl, araliphatic, heteroaryl, heteroaraliphatic, heterocyclyl or heterocyclyl-aliphatic radical or (b) a divalent phenylene or $C_1$–$C_4$ alkylene group joined to the

ring so as to form a bridged polycyclic group; and

represents a quaternized nitrogen-containing non-aromatic heterocycle.

U.K. Patent Application No. 2,128,187A discloses carbapenem antibiotics characterized by a 2-substituent of the formula

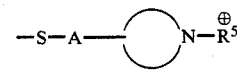

in which A represents a $C_1$–$C_6$ straight or branched chain alkylene group; $R^5$ represents an optionally substituted aliphatic, cycloaliphatic, cycloaliphatic-aliphatic, aryl, araliphatic, heteroaryl, heteroaraliphatic, heterocyclyl or heterocyclyl-aliphatic radical and

represents a nitrogen-containing aromatic heterocycle attached to the alkylene group A at a ring carbon atom and quaternized by substituent $R^5$.

U.K. Patent Application No. 2,118,183A discloses carbapenem antibiotics characterized by a 2-substituent of the formula

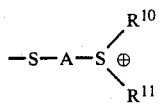

wherein A represents a $C_2$–$C_6$ straight or branched chain alkylene group and $R^{10}$ and $R^{11}$ each independently represents optionally substituted aliphatic, cycloaliphatic, cycloaliphatic-aliphatic, aryl, heterocyclyl, heterocyclyl-aliphatic, heteroaryl or heteroaliphatic, or $R^{10}$ and $R^{11}$ taken together with the S⊕ to which they are attached represent an optionally substituted sulfur-containing heterocyclic ring. Example 1 of U.K. No. 2,118,183A discloses the carbapenem antibiotic of the formula

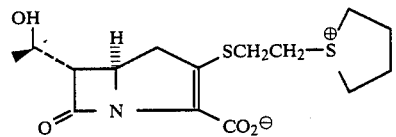

which differs from the compounds of the present application in that the heterocyclic group of the 2-substituent is bonded to the ethylene group via the sulfonium group.

Although there are a vast number of carbapenem derivatives disclosed in the literature, there is still a need for new carbapenems since known derivatives may be improved upon in terms of spectrum of activity, potency, stability and/or toxic side effects.

SUMMARY OF THE INVENTION

The present invention provides a novel series of carbapenem derivatives characterized by a 2-substituent of the formula

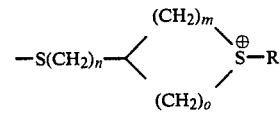

wherein n is 0, 1, 2, or 3, m is 1 or 2, o is 1 or 2, and R is $C_1$–$C_6$ alkyl, allyl, propargyl, carboxymethyl, cyanomethyl or aralkyl where the aryl moiety is phenyl or heteroaryl and the alkyl moiety is $C_1$–$C_6$ alkyl, said heterocyclic ring containing the sulfonium group being optionally substituted at a ring carbon atom or atoms by one or two $C_1$–$C_6$ alkyl groups. More specifically, the present invention provides carbapenem derivatives of the formula

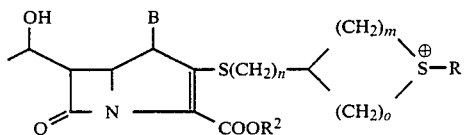

wherein $R^2$ is hydrogen or a conventional readily removable carboxyl protecting group, B is hydrogen or methyl, n is 0, 1, 2, or 3, m is 1 or 2, o is 1 or 2 and R is $C_1$–$C_6$ alkyl, allyl, propargyl, carboxymethyl, cyanomethyl or aralkyl in which the aryl moiety is phenyl or a 5–6 membered heteroaryl group and the alkyl moiety is $C_1$–$C_6$ alkyl, said heterocyclic ring containing the sulfonium group being optionally substituted at a ring carbon atom or atoms by one or two $C_1$–$C_6$ alkyl groups; or pharmaceutically acceptable salts or physiologically hydrolyzable esters thereof. The compounds of formula I are potent antibacterial agents characterized by unusually high gram-negative activities, particularly for species of Pseudomonas, or are intermediates useful in the preparation of such agents.

Also included in the present invention are processes for preparing the novel carbapenem derivatives described above and pharmaceutical compositions containing the biologically active carbapenem derivatives in combination with pharmaceutically acceptable carriers or diluents.

DETAILED DESCRIPTION

The novel compounds of general formula I above contain the carbapenem nucleus

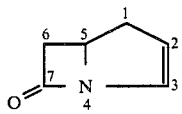

and may thus be named as 1-carba-2-penem-3-carboxylic acid derivatives. Alternatively, the compounds may be considered to have the basic structure

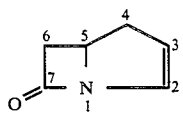

and named as 7-oxo-1-azabicyclo(3.2.0)hept-2-ene-2-carboxylic acid derivatives. While the present invention includes compounds wherein the relative stereochemistry of the 5,6-protons is cis as well as trans, the preferred compounds have the 5R,6S (trans) stereochemistry as in the case of thienamycin.

The compounds of formula I may be unsubstituted at the 1-position (B=hydrogen) or substituted by a methyl group. The methyl substituent may be in either the α- or β-configuration, and it is intended that the present invention include the individual α- and β-isomers, as well as mixtures thereof. The most preferred 1-substituted compounds are those having the β-configuration.

The hydroxyethyl substituent at the 6-position of the carbapenem nucleus most preferably has the absolute configuration 5R, 6S, 8R.

The 2-substituent of the compounds of the present invention is characterized by a 4–6 membered heterocyclic ring containing a sulfonium functional group, said ring being linked through a carbon atom either to an alkylene group or directly to the sulfur atom attached to the carbapenem nucleus.

The 4–6 membered heterocyclic group containing the sulfonium group may be optionally substituted at a ring carbon atom or atoms by one or two $C_1$–$C_6$ alkyl groups. Preferred substituted rings are those of the formula

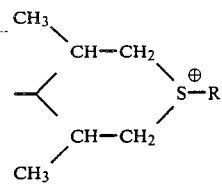

and

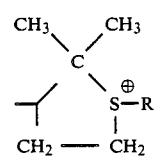

The R substituent of the sulfur-containing heterocyclic ring may be straight or branched-chain $C_1$–$C_6$ alkyl, preferably $C_1$–$C_4$ alkyl, and most preferably $C_1$–$C_2$ alkyl, allyl, propargyl, carboxymethyl, cyanomethyl or aralkyl. The aryl moiety of the aralkyl group may be phenyl or a 5–6 membered heteroaryl group. The term "heteroaryl" as used herein refers to an aromatic ring having 1–3 hetero atoms independently selected from O, S, and N and the alkyl moiety of the aralkyl group is straight or branched chain $C_1$–$C_6$ alkyl, preferably $C_1$–$C_4$ alkyl and most preferably $C_1$–$C_2$ alkyl. Examples of suitable heteroaryl groups include thienyl, and furyl.

Compounds of formula I may exist in the form

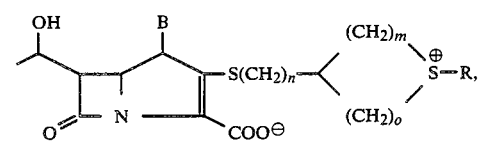

in the form

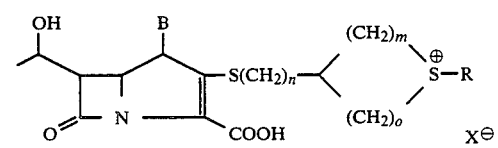

or in the form

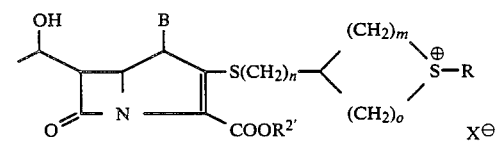

in which B, n, m, o, and R are as defined above, $R^{2'}$ is a conventional readily removable carboxyl protecting group and $X^\ominus$ is a counter ion. The counter ion, in the case of biologically active end-products, is selected so as to provide pharmaceutically acceptable salts for therapeutic administration or, in the case of intermediate compounds of formula I, $X^{\ominus}$ may also be a toxic ion. In such case the ion can be subsequently removed or substituted by a pharmaceutically acceptable ion to form an active end product for therapeutic use.

The term "conventional readily removable carboxyl protecting group" refers to a known ester group which has been employed to block a carboxyl group during the chemical reaction steps described below and which can be removed, if desired, by methods which do not result in any appreciable destruction of the remaining portion of the molecule, e.g. by chemical or enzymatic hydrolysis, treatment with chemical reducing agents under mild conditions, irradiation with ultraviolet light or catalytic hydrogenation. Examples of such ester protecting groups include benzhydryl, allyl, p-nitrobenzyl, 2-naphthylmethyl, benzyl, trichloroethyl, silyl such as trimethylsilyl, phenacyl, p-methoxybenzyl, acetonyl, o-nitrobenzyl, 4-pyridylmethyl and $C_1$–$C_6$ alkyl such as methyl, ethyl or t-butyl. Included within such protecting groups are those which are hydrolyzed under physiological conditions such as pivaloyloxymethyl, acetoxymethyl, phthalidyl, indanyl and methoxymethyl. Particularly advantageous carboxyl protecting groups are p-nitrobenzyl which may be readily removed by catalytic hydrogenolysis and allyl which may be removed with a catalyst comprising a mixture of a palladium compound and triphenylphosphine in an aprotic solvent such as tetrahydrofuran, diethyl ether, methylene chloride, ethyl acetate, or acetonitrile.

The pharmaceutically acceptable salts referred to above include the nontoxic acid addition salts, e.g. salts with mineral acids such as hydrochloric, hydrobromic, hydroiodic, phosphoric, sulfuric, etc. and salts with organic acids such as maleic, acetic, citric, succinic, benzoic, tartaric, fumaric, mandelic, ascorbic, lactic, gluconic, and malic.

Compounds of formula I wherein $R^2$ is hydrogen, an anionic charge or a physiologically hydrolyzable ester group together with pharmaceutically acceptable salts thereof are useful as antibacterial agents. The remaining compounds of formula I are valuable intermediates which can be converted into the above-mentioned biologically active compounds.

A preferred embodiment of the present invention comprises compounds of the formula

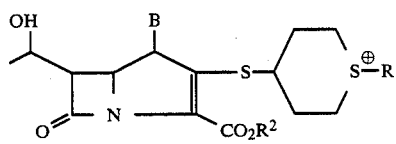

wherein B and R and $R^2$ are as defined above, and pharmaceutically acceptable salts or physiologically hydrolyzable esters thereof. Within this group of compounds, preferred R substituents are $C_1$–$C_6$ alkyl, especially methyl.

A most preferred embodiment of the present invention comprises the compounds

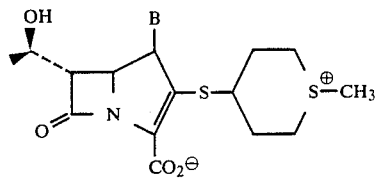

wherein B is hydrogen or β-methyl and pharmaceutically acceptable salts and esters thereof.

The carbapenem derivatives of general formula I are prepared from starting materials of the formula

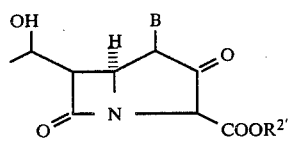

wherein B and $R^{2'}$ are as defined above. Compounds of formula III have been disclosed, for example, in European Patent Application Nos. 38,869 and 54,917 and may be prepared by the general methods described therein.

One process for preparing compounds I from starting materials III may be summarized by the following reaction scheme:

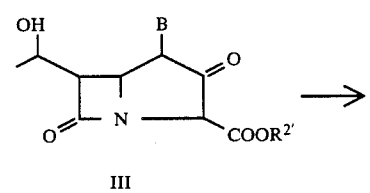

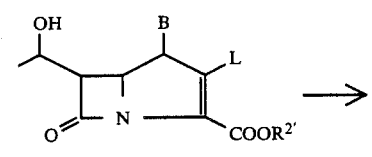

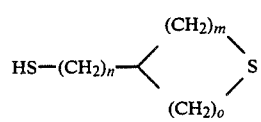

L = conventional leaving group

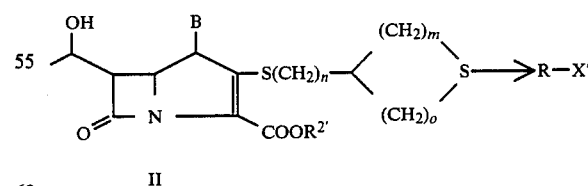

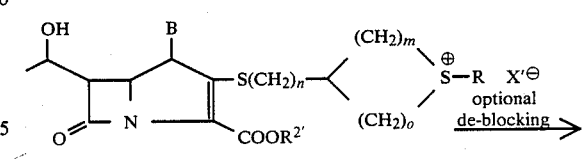

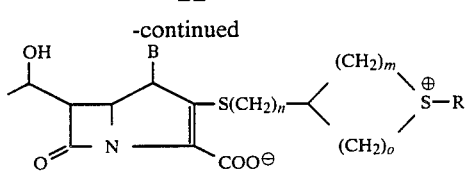

A preferred and alternate process for preparing compounds I from starting materials III may be summarized by the following scheme:

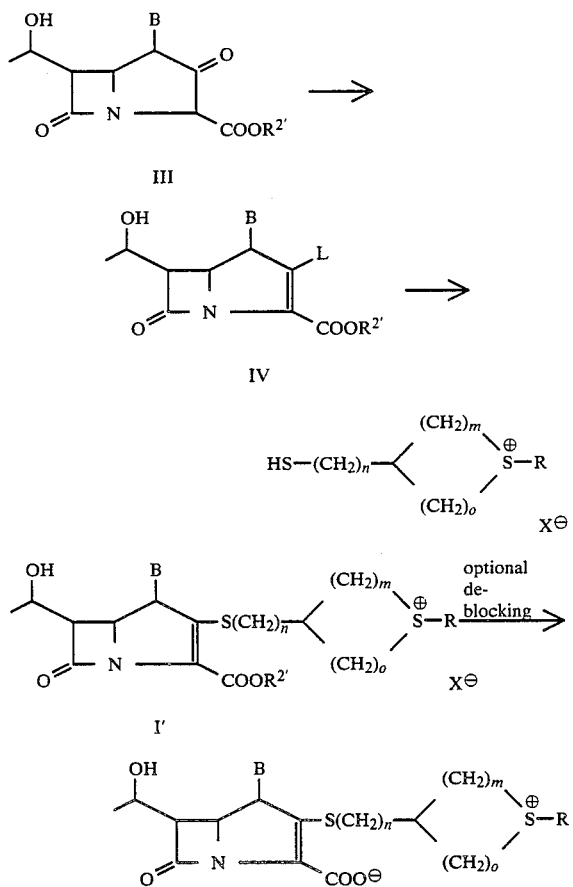

To elaborate on the first scheme described above, starting material III is reacted in an inert organic solvent such as methylene chloride, acetonitrile, or dimethylformamide with about an equimolar amount of an agent R°—L such as p-toluenesulfonic acid anhydride, p-nitrobenzene sulfonic acid anhydride, 2,4,6-triisopropylbenzenesulfonic acid anhydride, methanesulfonic acid anhydride, trifluoromethanesulfonic acid anhydride, diphenyl chlorophosphate, toluenesulfonyl chloride, p-bromobenzenesulfonyl chloride, or the like, wherein L is the corresponding leaving group such as toluenesulfonyloxy, p-nitrobenzenesulfonyloxy, diphenoxyphosphinyloxy, and other leaving groups which are established by conventional procedures and are well-known in the art. The reaction to establish the leaving group at the 2-position of intermediate III is advantageously carried out in the presence of a base such as diisopropylethylamine, triethylamine, 4-dimethylaminopyridine, or the like, at a temperature of from about −20° to +40° C., most preferably at about 0° C. The leaving group L of intermediate IV may also be halogen in which case such group is established by reacting intermediate III with a halogenating agent such as $\phi_3PCl_2$, $\phi PBr_2$, $(\phi O)_3PBr_2$, oxalylchloride or the like in a solvent such as $CH_2Cl_2$, $CH_3CN$, THF, or the like, in the presence of a base such as diisopropylethylamine, triethylamine, 4-dimethylaminopyridine, or the like. Intermediate IV may be isolated if desired, but is conveniently used for the next step without isolation or purification.

Intermediate IV is next converted to intermediate II by a conventional displacement reaction. Thus, intermediate IV may be reacted with approximately an equimolar amount of a thiol having the formula

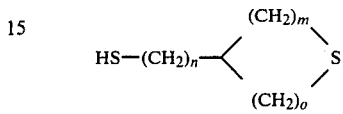

where n, m, and o are as defined above in an inert organic solvent such as dioxane, dimethylformamide, dimethylsulfoxide or acetonitrile and in the presence of a base such as diisopropylethylamine, triethylamine, sodium hydrogen carbonate, potassium carbonate or 4-dimethylaminopyridine. The temperature for the displacement is not critical, but an advantageous temperature range is from about −40° C. to 25° C. Most conveniently, the reaction is carried out with cooling, e.g. at about 0° C. to −10° C.

Quaternization of the ring sulfur in the heterocyclic 2-substituent of intermediate II is carried out by reacting intermediate II in an inert organic solvent with at least an equivalent (up to about a 50% molar excess) of an alkylating agent of the formula

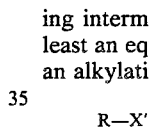

wherein R is as defined above and X' is a conventional leaving group such as halo (chloro, bromo or iodo most preferably iodo) or a sulfonate ester moiety such as a mesylate, tosylate or triflate. Examples of suitable non-reactive organic solvents are chloroform, methylene chloride, tetrahydrofuran, dioxane, acetone, dimethylsulfoxide and dimethylformamide. The temperature for the alkylation reaction is not critical and temperatures in the range of from about 0° C. to 40° C. are preferred. Most conveniently, the reaction step is carried out at room temperature.

Intermediate I' will have a counter ion X' (e.g. derived from the alkylating agent used) associated with it which at this stage or at a later stage, i.e. following the de-blocking step, may be substituted by a different counter ion, e.g. one which is more pharmaceutically acceptable, by conventional procedures. Alternatively, the counter ion may be subsequently removed during the de-blocking step.

The de-blocking step to remove the carboxyl protecting group $R^{2'}$ of intermediate I' is accomplished by conventional procedures such as solvolysis, chemical reduction or hydrogenation. Where a protecting group such as p-nitrobenzyl, benzyl, benzhydryl or 2-naphthylmethyl is used which can be removed by catalytic hydrogenation, intermediate I' in a suitable solvent such as dioxane-water-ethanol, tetrahydrofuran-aqueous dipotassium hydrogen phosphate-isopropanol or the like may be treated under a hydrogen pressure of from 1 to 4 atmospheres in the presence of a hydrogenation catalyst such as palladium on charcoal, palladium hydroxide, platinum oxide or the like at a temperature of from 0° to 50° C. for from about 0.24 to 4 hours. When $R^{2'}$ is a group such as o-nitrobenzyl, photolysis may also be used for deblocking. Protecting groups such as 2,2,2-trichloroethyl may be removed by mild zinc reduction. The allyl protecting group may be removed with a catalyst comprising a mixture of a palladium compound and triphenylphosphine in an aprotic solvent such as tetrahydrofuran, diethyl ether or methylene chloride. Similarly, other conventional carboxyl protecting groups may be removed by methods known to those skilled in the art. Finally, as mentioned above, compounds of formula I' where $R^{2'}$ is a physiologically hydrolyzable ester such as acetoxymethyl, phthalidyl, indanyl, pivaloyloxymethyl, methoxymethyl, etc. may be administered directly to the host without de-blocking since such esters are hydrolyzed in vivo under physiological conditions.

In a variant of the above process, the carboxyl protecting group of intermediate II may be removed prior to the quaternization step. Thus, the carboxyl protecting group is removed as described above to give the corresponding free carboxylic acid and the free acid is then quaternized with alkylating agent R—X' to give the desired quaternized product of formula I. When the de-protected intermediate is quaternized, the solvent may be water or a non-reactive organic solvent, or mixtures thereof. Examples of suitable solvents include water, organic solvents such as chloroform, methylene chloride, tetrahydrofuran, dioxane, acetone, dimethylsulfoxide and dimethylformamide and water-organic solvent mixtures such as water-acetone or water-dimethylformamide. The temperature for the quaternization reaction is not critical and temperatures in the range of from about −40° C. to about room temperature may be conveniently employed. Most advantageously, the reaction is carried out at about 0° C.

In the second-described and preferred process shown above, an intermediate of the formula

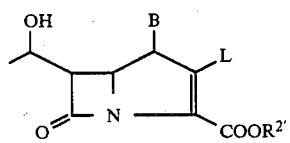

wherein B, L, and $R^{2'}$ are as defined above is reacted with a thiol compound of the formula

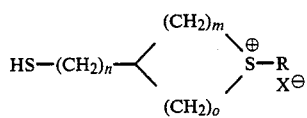

wherein n, m, o. R, and $X^\beta$ are as defined above in an inert solvent and in the presence of base to produce a carbapenem product of formula I' and, if desired, the carboxyl protecting group $R^{2'}$ is removed to give the corresponding de-blocked compound of formula I, or a pharmaceutically acceptable salt thereof.

In this process there is utilized the intermediate of the formula

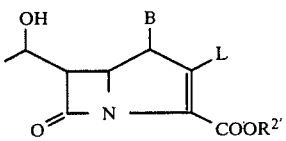

which, as mentioned above, has been disclosed, for example, in European Patent Application Nos. 38,869 and 54,917 and which may be prepared by the general methods described therein. L represents a conventional leaving group (defined as "X" in European Patent Application No. 38,869) such as chloro, bromo, iodo, benzenesulfonyloxy, p-toluenesulfonyloxy, p-nitrobenzenesulfonyloxy, methanesulfonyloxy, trifluoromethanesulfonyloxy, diphenoxyphosphinyloxy or di(trichloroethoxy)phosphinyloxy. The preferred leaving group is diphenoxyphosphinyloxy.

Intermediates of formula IV are generally formed in situ by reacting an intermediate of the formula

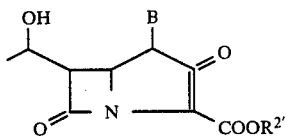

with a suitable acylating agent R°—L. The preferred intermediate IV where L is diphenoxyphosphinyloxy may be prepared by reacting keto ester III in an inert organic solvent such as methylene chloride, acetonitrile or dimethylformamide with about an equimolar amount of diphenyl chlorophosphate in the presence of a base such as diisopropylethylamine, triethylamine, 4-dimethylaminopyridine or the like at a temperature of from about −20° C. to +40° C., most preferably at about 0° C. Intermediate IV may be isolated if desired, but is conveniently used as the starting material for this process without isolation or purification.

Carbapenem intermediate IV is reacted with a thiol compound of the formula

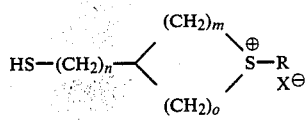

wherein n, m, o, and R are as defined above and $X^-$ is a counter ion. The reaction is carried out in an inert solvent such as acetonitrile, acetonitrile-dimethylformamide, tetrahydrofuran, tetrahydrofuran-$H_2O$, acetonitrile-$H_2O$, dimethylacetamide, dimethylacetamide-$H_2O$ or acetone in the presence of base. The nature of the base is not critical. Suitable bases include sodium hydroxide, diisopropylethylamine, 1,8-diazabicyclo[5.4.0]undec-7-ene, 1,5-diazabicyclo[4.3.0]non-5ene and tri($C_1$-$C_4$) alkylamines such as triethylamine, tributylamine, or tripropylamine. The reaction may be carried out over a wide temperature range, e.g. −15° C. up to room temperature, but is preferably done at a temperature in the range of from about −15° C. to +15° C., most preferably at around 0° C.

The carbapenem product produced by reaction of the thiol with intermediate IV will have a counter ion associated with it [e.g. $(C_6H_5O)_2PO_2^-$, $Cl^-$ or the anion associated with the quaternary thiol] which may at this stage be substituted by a different counter anion, e.g. one which is more pharmaceutically acceptable, by conventional procedures. Alternatively, the counter ion may be removed during the subsequent de-blocking step. Where the quaternized carbapenem compound and counter ion form an insoluble product, the product may crystallize out as it is formed and be collected pure by filtration.

Following formation of the desired carbapenem product, the carboxyl protecting group $R^{2'}$ of Compound I' may be optionally removed by conventional procedures such as solvolysis, chemical reduction or hydrogenation. Where a protecting group such as p-nitrobenzyl, benzyl, benzhydryl or 2-naphthylmethyl is used which can be removed by catalytic hydrogenation, intermediate I' in a suitable solvent such as dioxane-water-ethanol, tetrahydrofurandiethylether-buffer, tetrahydrofuran-aqueous dipotassium hydrogen phosphate-isopropanol or the like may be treated under a hydrogen pressure of from 1 to 4 atmospheres in the presence of a hydrogenation catalyst such as palladium on charcoal, palladium hydroxide, platinum oxide or the like at a temperature of from 0° to 50° C. for from about 0.24 to 4 hours. When $R^{2'}$ is a group such as o-nitrobenzyl, photolysis may also be used for deblocking. Protecting groups such as 2,2,2-trichloroethyl may be removed by mild zinc reduction. The allyl protecting group may be removed by using a catalyst comprising a mixture of a palladium compound and triphenyl phosphine in a suitable aprotic solvent such as tetrahydrofuran, methylene chloride or diethyl ether. Similarly, other conventional carboxyl protecting groups may be removed by methods known to those skilled in the art. Finally, as mentioned above, compounds of Formula I' where $R^{2'}$ is a physiologically hydrolyzable ester such as acetoxymethyl, phthalidyl, indanyl, pivaloyloxymethyl, methoxymethyl, etc., may be administered directly to the host without de-blocking since such esters are hydrolyzed in vivo under physiological conditions.

The quaternary thiol intermediates may be prepared by reacting a protected thiol of the formula

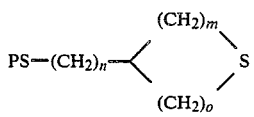

wherein P is a conventional thiol protecting group in an inert organic solvent such as diethyl ether, dichloromethane, methylene chloride, dioxane, benzene, xylene, toluene, or mixtures thereof with a suitable alkylating agent of the formula

wherein R is as defined above and X' is a conventional leaving group such as halo (chloro, bromo, or iodo, most preferably iodo) or a sulfonate ester moiety such as mesylate, tosylate, or triflate. The temperature for the alkylation reaction is not critical, and temperatures in the range of from about 0° C. to 40° C. are preferred.

The protecting group P is a conventional thiol protecting group such as the protecting groups disclosed in Chapter 6 of *Protective Groups in Organic Synthesis*, Theodora W. Greene, John Wiley and Sons, New York, 1981, pg. 193–217. Examples of suitable thiol protecting groups include thioethers such as benzyl, 4-methylbenzyl, 3,4-dimethylbenzyl, p-methoxybenzyl, o-hydroxybenzyl, p-hydroxybenzyl, acetoxybenzyl, p-nitrobenzyl or diphenylmethyl and thioesters such as acetyl, benzoyl or thiobenzoyl. A preferred protecting group is acetyl which may be removed by treatment with aqueous base before reaction with intermediate IV.

As in the case of other β-lactam antibiotics, compounds of general formula I may be converted by known procedures to pharmaceutically acceptable salts which, for purposes of the present invention, are substantially equivalent to the non-salted compounds. Thus, for example, one may dissolve a compound of formula I wherein $R^2$ is an anionic charge in a suitable inert solvent and then add an equivalent of a pharmaceutically acceptable acid. The desired acid addition salt may be recoved by conventional procedures, e.g. solvent preciptation, lyophilization, etc.

It will be appreciated that certain products within the scope of formula I may be formed as optical isomers as well as epimeric mixtures thereof. It is intended that the present invention include within its scope all such optical isomers and epimeric mixtures. For example, in the case of the hydroxyethyl 6-substituent, such substituent may be in either the R or S configuration and the resulting isomers as well as epimeric mixtures thereof are encompassed by the present invention.

A compound of formula I where $R^2$ is hydrogen or an anionic charge, or a pharmaceutically acceptable salt thereof may also be converted by conventional procedures to a corresponding compound where $R^2$ is a conventional carboxyl protecting group may be converted to the corresponding compound where $R^2$ is hydrogen, an anionic charge or a physiologically hydrolyzable ester group, or a compound of formula I wherein $R^2$ is a conventional carboxyl protecting group may be converted to the corresponding compound where $R^2$ is hydrogen, an anionic charge or a physiologically hydrolyzable ester group, or a pharmaceutically acceptable salt thereof.

The novel carbapenem derivatives of general formula I wherein $R^2$ is hydrogen, an anionic charge or a physiologically hydrolyzable carboxyl protecting group, or the pharmaceutically acceptable salts thereof, are potent antibiotics active against various gram-positive and gram-negative bacteria and they may be used, for example, as animal feed additives for promotion of growth, as preservatives in food, as bactericides in industrial applications, for example in waterbased paint and in the white water of paper mills to inhibit the growth of harmful bacteria, and as disinfectants for destroying or inhibing the growth of harmful bacteria on medical and dental equipment. They are especially useful, however, in the treatment of infectious disease in humans and other animals caused by gram-positive or gram-negative bacteria.

The pharmaceutically active compounds of this invention may be used alone or formulated as pharmaceutical compositions comprising, in addition to the active carbapenem ingredient, a pharmaceutically acceptable carrier or diluent. The compounds may be administered by a variety of means; those of principal interest include; orally, topically or parenterally (e.g. intravenous or intramuscular injection). The pharmaceutical compositions may be in solid form such as capsules, tablets, powders, etc. or in liquid form such as solutions, suspensions or emulsions. Compositions for injection, the preferred route of delivery, may be prepared in unit dose ofrm in ampules or in multidose containers and may contain formulatory agents such as suspending, stabilizing and dispersing agents. The compositions may be in ready to use form or in powder form for reconstitution at the time of delivery with a suitable vehicle such as sterile water.

The dosage to be administered depends to a large extent on the particular compound being used, the particular composition formulated, the route of administration, the nature and condition of the host and the particular situs and organism being treated. Selection of the particular preferred dosage and route of application, then, is left to the discretion of the therapist. In general, however, the compounds may be administered parenterally or orally to mammalian hosts in an amount of from about 5 to 200 mg/kg/day. Administration is generally carried out in divided doses, e.g. three to four times a day.

To illustrate the potent broad-spectrum antibacterial activity of the carbapenems of the present invention, biological data is provided below relating to the presently preferred carbapenem compound of the present invention.

In Vitro Activity

The carbapenem compound prepared in Example 1 after solution in water and dilution with Nutrient Broth was found to exhibit the following Minimum Inhibitory Concentrations (M.I.C.) in mcg/ml versus the indicated microorganisms as determined by overnight incubation at 37° C. by tube dilution.

In Vitro Antibacterial Activity of Carbapenem Derivative of Example

| Organism | | MIC (mcg/ml) BMY-25039 | |
|---|---|---|---|
| | | Lot# 1794-20 | Lot# 1794-27 |
| S. pneumoniae | A-9585 | 0.001 | 0.002 |
| S. pyogenes | A-9604 | 0.004 | 0.004 |
| S. faecalis | A20688 | 0.5 | 0.5 |
| S. aureus | A-9537 | 0.008 | 0.008 |
| S. aureus, 50% serum | A-9537 | 0.016 | 0.016 |
| S. aureus (Penicillin-resistant) | A-9606 | 0.016 | 0.03 |
| S. aureus (Methicillin-resistant) | A15097 | — | — |
| E. coli | A15119 | 0.008 | 0.016 |
| E. coli | A20341-1 | 0.016 | 0.03 |
| K. pneumoniae | A-9664 | 0.03 | 0.06 |
| K. pneumoniae | A20468 | 0.06 | 0.25 |
| E. cloacae | A-9659 | 0.06 | 0.25 |
| E. cloacae | A-9656 | 0.06 | 0.25 |
| P. mirabilis | A-9900 | 0.016 | 0.016 |
| P. vulgaris | A21559 | 0.016 | 0.016 |
| M. morganii | A15153 | 0.06 | 0.06 |
| P. rettgeri | A22424 | 0.13 | 0.13 |
| S. marcescens | A20019 | 0.03 | 0.03 |
| P. aeruginosa | A-9843A | 2 | 2 |
| P. aeruginosa (Carbenicillin-resistant) | A21213 | 0.25 | 0.25 |

Blood Levels

For the determination of blood levels, two groups of mice were used. Each group consisted of four 20 g mice. Prior to dosing (5–10 min.) one of the groups received an i.p. injection of a dipeptidase inhibitor (BCH-1) at a level of 10 mg/kg. At intervals of 10, 20, 30, 40, 45, 60 and 90 minutes after dosing intramuscularly with the compound of Example 1, blood samples were removed from each mouse and assayed for biological activity using sensitive assay plates containing $B.$ $subtilis$ ATCC 6633.

$$\underset{H}{\overset{H_3C}{\diagdown}} C = \underset{COOH}{\overset{NHCO\text{—}\!\!\!\diagup\!\!\!\!\diagdown\text{—}}{\diagup}} \quad \text{BCH-1}$$

| Compound | BCH-1 (10 mg/kg) i.p. | C max (μg/ml) | Half-life (min) | Tmax (min) | AUC (μg.hr) ml |
|---|---|---|---|---|---|
| Ex. 1 | — | 15.4 | 9 | 10 | 6.8 |
| | + | 16.1 | 10 | 20 | 10.9 |

| Compound | BCH-1 i.p. | Blood Levels (μg/ml) Min. after Administration at 20 mg/kg i.m. | | | | | |
|---|---|---|---|---|---|---|---|
| | | 10 | 20 | 30 | 45 | 60 | 90 |
| Ex. 1 | — | 15.4 | 11.4 | 7.2 | 2.9 | 0.7 | 0.3 |
| | + | 15.4 | 16.1 | 12.6 | 7.4 | 3.0 | 0.3 |

Urinary Recovery

Two groups of mice were used for the urinary recovery evaluation. Each group consisted of four 20 g mice. Prior to dosing (5–10 minutes) one of the groups received an i.p. injestion of a dipeptidase inhibitor (BCH-1) at a level of 10 mg/kg. Following dosing, animals were placed in individual metabolism cages and the urine collected over ice at intervals of 0–3 and 3–6 hr. Animals were fasted overnight and a dextrose-amino acid solution was available ad libitum starting one hour before drug administration through six hours of urine collection. Urine samples were assayed for biological activity using sensitive assay plates containing $B.$ $subtilis$ ATCC 6633.

| Compound | BCH-1 10 mg/kg i.p. | Percent Recovered | | |
|---|---|---|---|---|
| | | 0–3 hr. | 3–6 hr. | 0–6 hr. |
| Ex. 1 | — | 44 | 0.2 | 44.2 |
| | + | 67 | 0.1 | 67.1 |

In Vivo Activity

Challenge Preparation:

BHI broth (9.0 ml) was inoculated with a loopful of thawed stock suspension of P. aeruginosa A9843a and incubated for 18 hr at 37° C. A volume of 0.5 ml of the 18 hr culture was added to 20 ml BHI broth and incubated for 3 hr. with constant shaking at 37° C. A 1/10,000 dilution of the shaker culture was prepared in 0.4% hog gastric mucin. Mice were infected by the intraperitoneal route with 0.5 ml of the bacterial suspension (corresponding to $6.0 \times 10^4$ viable cells/mouse).

Determination of 50% protective dose/PD$_{50}$):

Infected mice were treated intramuscularly with various doses of the compound of Example 1 immediately following infection and again at 2 hour post-infection. Each mouse received a volume of 0.2 ml intramuscularly. Deaths were recorded over a period of five days following infection at which time the PD$_{50}$ for the compound was determined by estimation of the 50% endpoint using the probit analysis plot.

The PD$_{50}$ i.m. was determined to be 0.71 mg/kg.

Illustrative examples of the preparation of compounds of the present invention follow. These examples are given in illustration of, but not in limitation of, the present invention.

EXAMPLE 1

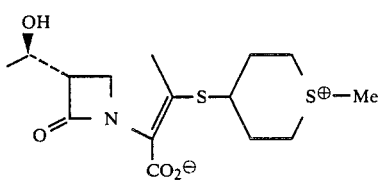

(5R,6S)-6-(1R—hydroxyethyl)-7-oxo-3-(1-methyl-4-thia-tetrahydrothiopyranium)-1-azabicyclo[3.2.0]-hept-2-ene-2-carboxylate

A.
4-Mercapto-1-Methyl-tetrahydrothiopyraniumtriflate

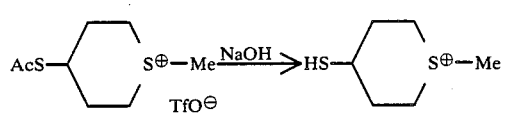

A cold (ice bath) aqueous solution (4 mL) of 4-acetylthio-1-methyl-tetrahydrothiopyraniumtriflate* (500 mg, 1.47 mmol) was treated with a 1M NaOH solution (2 mL, 2 mmol). The mixture was stirred for ca. 1 h. until all the starting material had disappeared on TLC (reversed phase silica gel). The pH of the strongly basic solution was brought to pH 7.5 with 10% HCl. This thiol was used as such for the next coupling reaction with the enol phosphate.

*4-acetylthio-tetrahydrothiopyran (1.1 g, 6.25 mmol) was quaternized with methyl triflate (1.1 mL) in methylene chloride at (0° C.) to give the corresponding quaternized derivative (2.16 g, 6.34 mmol, 98.6%).

B.
p-Nitrobenzyl(5R,6S)-6-(1-R-hydroxyethyl)-7-oxo-3-(1-methyl-4-thia-tetrahydrothiopyranium diphenylphosphate)-1-azabicyclo[3.2.0]hept-2-ene-2-carboxylate

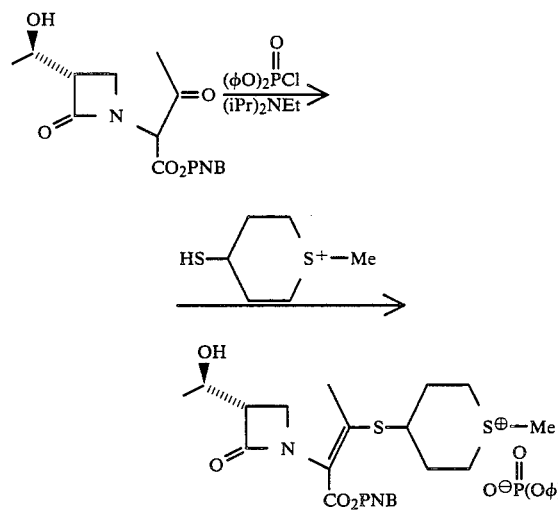

A solution of enol phosphate made from p-nitrobenzyl (5R-hydroxyethyl)-3,7-dioxo-1-azabicyclo[3.2.0-]hept-2-ene-3-carboxylate (174 mg, 0.500 mmol) diisopropylethylamine (105 μL, 0.603 mmol) and diphenylchlorophosphate (124 μL, 0.598 mmol) in acetonitrile (4 mL) at 0° C. (1 h) was treated with cold 4-mercapto-1-methyl-tetrahydrothiopyraniumtriflate (from 500 mg of the corresponding 4-acetylthio derivative). Cold acetonitrile (ca. 20 mL) was added until a phase mixture was obtained. The solution was stirred at 0° C. for 2 h, kept at −78° C. for 18 h and stirred again for 4 h at 0°; the pH being kept at 7.8 by the addition of aqueous NaHCO₃. Acetonitrile was evaporated at low temperature <15° C. to give an aqueous fraction and a precipitated gum. The aqueous fraction was poured on a silica gel reversed phase column. (2.5×8 cm int.). The polarity of the eluent was increased with CH₃CN. The resulting gum was eventually dissolved in (≈10% CH₃CN/H₂O) and passed through the column. Title compound was eluted with a mixture of 15%+30% CH₃CN in H₂O. Acetonitrile was evacuated under high vacuum at ≈0°-5° C. for 1 h. Lyophilization of the aqueous fraction gave a yellow powder (240 mg, 67%); ir (nujol) $v_{max}$: 1772 (s, β-lactam C=O) and 1595 cm$^{-1}$ (s, CO₂⁻); ¹Hmr (80 MHz, D₂O) δ: 8.28, 8.17, 7.68, 7.57 (4H, m, aromatic H), 7.57–7.11 (10H, m, aromatic H); 5.39 (2H, b.s., O—CH₂—), 4.45–4.10 (2H, m, H-1' and H-5); 3.95–3.00 (7H, m, CH₂—4, CH₂—S⁺CH₂, S—CH); 2.88, 2.87 (3H, 2s, >S⁺—CH₃), 2.75–1.75 (4H, m, CH₂CH—CH₃) and 1.25 ppm (3H, d, J=6.4, CH₃).

EXAMPLE 2

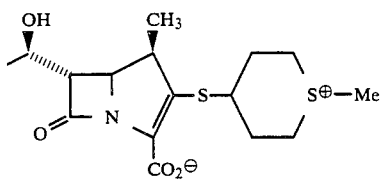

(5R,6S)-6-(1R-hydroxyethyl)-4R-methyl-3-(1-methyl-4-thiatetrahydrothiopyranium)-7-oxo-1-azabicyclo[3.2.0]-hept-2-ene-2-carboxylate

A. Preparation of 4-acetylthio-1-methyltetrahydrothiopyranium trifluoromethanesulfonate

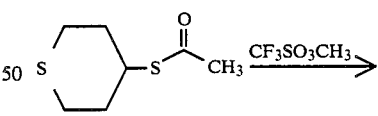

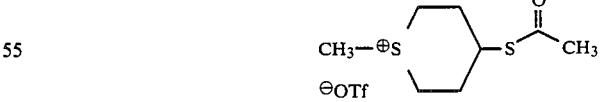

To a cooled (5° C.) solution of 4-acetylmercaptotetrahydrothiopyran (1.91 g, 10.9 mmol) in dichloromethane (20 mL) was added methyltrifluoromethanesulfonate (1.3 mL, 11.5 mmol) dropwise over 30 minutes. The solvent was removed in vacuo to give 3.85 g (>100%) of the title compound as an oil which was used as such: ¹Hmr (D₂O) δ: 2.14–3.79 (m, 8H, ring protons), 2.39 (s, 3H, COCH₃), 2.93 (s, 3H, SCH₃) and 5.46 ppm (s, 1H, CHS).

B. Preparation of 4-mercapto-1-methyl-tetra-hydrothiopyranium trifluoromethanesulfonate

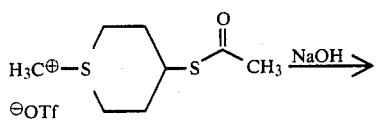

To a cooled (5° C.) solution of 4-acetylthio-1-methyl-tetrahydrothiopyranium trifluoromethanesulfonate (3.35 g, 9.83 mmol) in deoxygenated water (32 mL) was added a solution of 1M NaOH (10.8 mL, 10.8 mmol) dropwise. After stirring for 1 hr at 0° C., the pH was adjusted to 7.5 with 1N HCl. The solution was lyophylized to give the desired thiol plus a mixture of salts. The product was used as such without further purification: $^1$Hmr (D2$^O$) δ: 2.0–4.0 (m, 11H), 2.90 (s, 3H, SCH$_3$) and 1.9 ppm (s, 3H, CH$_3$CO$^-$).

C. Preparation of (5R, 6S) p-nitrobenzyl-6-(1$^1$R-hydroxyethyl)-4R-methyl-3-(1-methyl-4-thiatetrahydrothiopyranium)-7-oxo-1-azabicyclo[3.2.0]hept-2-ene-2carboxyl-diphenylphosphate

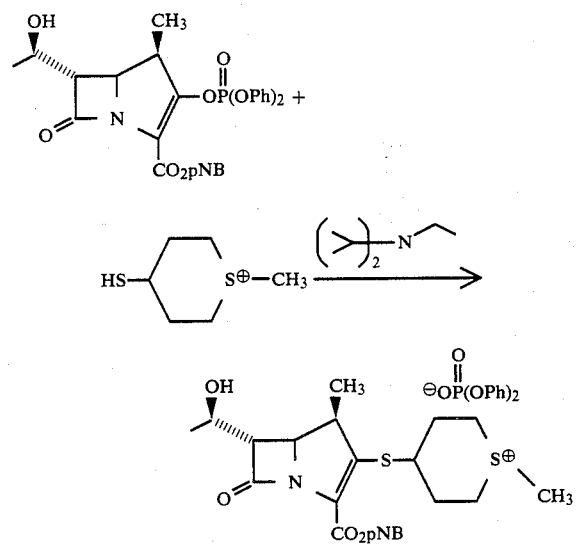

To a cooled (5° C.) solution of freshly prepared (5R, 6S)p-nitrobenzyl 3-diphenyl phosphate-4R-methyl-7-oxo-1-azabicyclo[3.2.0]hept-2-ene-2-carboxylate$^a$ (3.27 g, 5.5 mmol) in N,N-dimethylformamide (20 mL) under N$_2$ atmosphere was added a suspension of 1-methyl-4-mercaptotetrahydrothiopyranium trifluoromethane-sulfonate (2.7 g, 9.0 mmol) in N,N-dimethylformamide (10 mL) followed by N,N-diisopropylethylamine (1.57 mL, 9.0 mmol). After stirring for 1 hr at 5° C., the mixture was triturated with an ether-pet. ether (1:1, 210 mL) mixture and the oily layer was diluted with a water-acetonitrile mixture (8:1, 210 mL). The solution was washed with ether (2×100 mL) and the aqueous phase was applied on a reversed phase column (containing 200 g μBondapak C18 silica gel) eluting first with water (500 mL) then with a mixture of acetonitrile-water (10%, 20%, 30%, 500 mL each). After freeze drying, 2.4 g (58.6%) of the title compound was obtained: ir (nujol) ν$_{max}$: 1765 (CO β-lactam), 1705 cm$^{-1}$ (CO ester); $^1$Hmr (acetone-d$_6$) δ: 1.2 (d, 6H, CH$_3$CHOH and CH$_{3-4}$), 2.12–3.32 (m, 4H), 3.10 (s, 3H, SCH$_3$), 3.37–4.55 (m, 9H), 5.42 (q, J-14 Hz, CH$_2$Ar), 6.89–8.34 ppm (m, ArH).

$^a$This compound was prepared in the usual way starting from (5R, 6S)p-nitrobenzyl-6-(1$^1$R-hydroxyethyl)-3,7-dioxo-4R-methyl-1-azabicyclo[3.2.0]heptane-2-carboxylate, however, the enol phosphate was isolated by concentrating the reaction mixture under vacuum, diluting with an ethyl acetate-ether (1:1) mixture and washing with water. After drying over anhydrous magnesium sulfate, charcoalizing and removal of the solvent in vacuo, the pure compound was obtained quantitatively.

D. Preparation of (5R,6S)-6(1$^1$R-hydroxyethyl-4R-methyl-3-(1-methyl-4-thiatetrahydrothiopyranium)-7-oxo-1-azabicyclo[3.2.0-]hept-2-ene-2-carboxylate

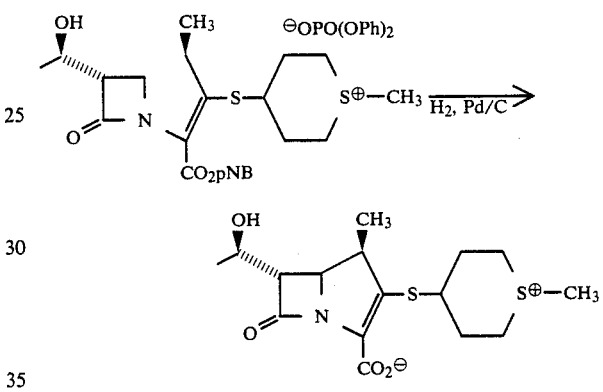

To a cooled (5° C.) solution of (5R,6S)p-nitrobenzyl-6-(1$^1$R-hydroxyethyl)-4R-methyl-3-(1-methyl-4-thiatetrahydrothiopyranium)-7-oxo-1-azabicyclo[3.2.0]hept-2-ene-2-carboxyl-diphenylphosphate (2.40 g, 3.23 mmol) in tetrahydrofuran (240 mL) and 0.05M pH 7.0 phosphate buffer (240 mL) was added ether (240 mL) and 10% Pd/C (2.4 g). The mixture was hydrogenated in a Paar apparatus at 45 psi H$_2$ at 15° C. for 1 hour. The solution was then filtered through glass fiber paper and the catalyst was washed with water (25 mL). The aqueous phase of the filtrate was washed with ether (2×100 mL) and purged under vacuum to remove any trace of organic solvent. The product was purified by reversed phase chromatography on μBondapak C-18 silica gel (100 g) using mixtures of acetonitrile-water as the eluent (10% CH$_3$CN—H$_2$O, quantity mL; 0%, 500 mL; 2%, 500 mL; 4%, 500 mL; 10%, 250 mL) to give 1.08 g of impure proudct. After lyophilization, this product and a 0.020 g sample from another experiment (starting from 0.067 mmol of the ester) was purified by hplc (hplc data re: C$_{18}$ μBondapak, using 5% CH$_3$CN—H$_2$O at 4 mL/min, R. I. detector) to give 328 mg. The product was repurified by reversed phase chromatography on silica gel (15 g, μBondapak C18 ) using water then 2% acetonitrile-water as the eluent to give 225 mg (19.1%) of the title compound as a white solid after lyophilization: uv (H$_2$O) λ$_{max}$: 298 nm (9581); ir (nujol) ν$_{max}$: 1750 (CO β-lactam), 1590 cm$^{-1}$ (CO carboxylate); $^1$Hmr (D$_2$O) δ: 1.21 (d, J=7.25 Hz, 3H, CH$_3$-4), 1.30 (d, J=6.37 Hz, 3H, CH$_3$CHOH), 1.92-2.64 (m, 4H, thiopyranyl protons), 2.94 (s, 3H, S—CH$_3$), 3.15-3.78 (m, 7H), 4.19–4.32 ppm (m, 2H); half-life evaluated to be 30 h at 37° C. in pH 7.4 biological buffer.

EXAMPLE 3

Following the general procedure of Example 1, the following compounds may be prepared by use of the appropriate starting materials.

25

-continued

[Structure: carbapenem with hydroxyethyl group, S-(CH₂)ₙ-Z substituent, COO⁻]

n = 0, 1, 2, 3

| Z = |
|---|
| tetrahydrothiophenium-S⁺-C₄H₉ |
| tetrahydrothiophenium-S⁺-C₅H₁₁ |
| tetrahydrothiophenium-S⁺-C₆H₁₃ |
| tetrahydrothiophenium-S⁺-CH(CH₃)₂ |
| tetrahydrothiophenium-S⁺-CH₂CH=CH₂ |
| tetrahydrothiophenium-S⁺-CH₂C≡CH |
| tetrahydrothiophenium-S⁺-CH₂COOH |
| tetrahydrothiophenium-S⁺-CH₂CN |
| tetrahydrothiophenium-S⁺-CH₂-phenyl |
| tetrahydrothiophenium-S⁺-CH₂CH₂-phenyl |
| tetrahydrothiophenium-S⁺-(CH₂)₆-phenyl |

26

-continued

[Structure: carbapenem with hydroxyethyl group, S-(CH₂)ₙ-Z substituent, COO⁻]

n = 0, 1, 2, 3

| Z = |
|---|
| tetrahydrothiophenium-S⁺-CH₂-thienyl (S) |
| tetrahydrothiophenium-S⁺-(CH₂)₆-thienyl (S) |
| tetrahydrothiophenium-S⁺-CH₂-furyl (O) |
| tetrahydrothiophenium-S⁺-(CH₂)₆-furyl (O) |
| thietanium-S⁺-CH₃ |
| thietanium-S⁺-C₃H₇ |
| thietanium-S⁺-C₂H₅ |
| thietanium-S⁺-C₄H₉ |
| thietanium-S⁺-C₅H₁₁ |
| thietanium-S⁺-C₆H₁₃ |
| thietanium-S⁺-CH(CH₃)₂ |

27
-continued
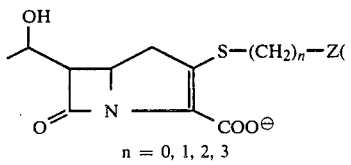
n = 0, 1, 2, 3
Z =
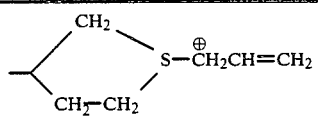
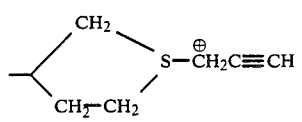
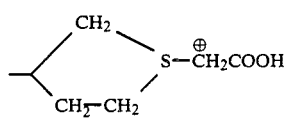
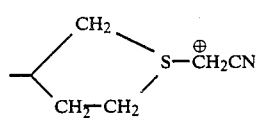
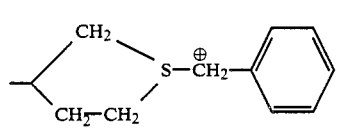
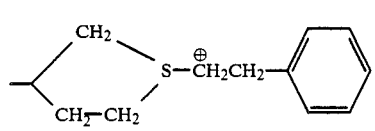
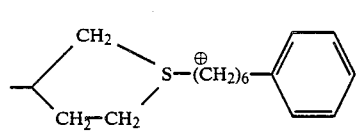
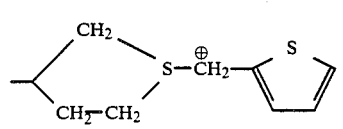
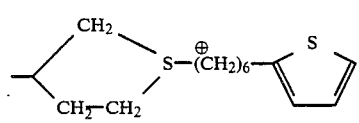
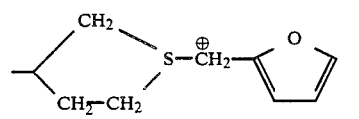
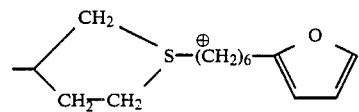
28
-continued
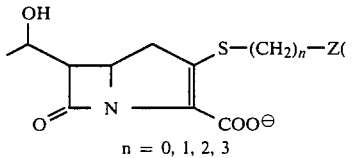
n = 0, 1, 2, 3
Z =
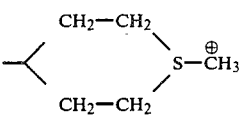
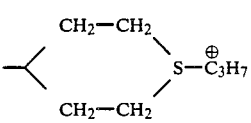
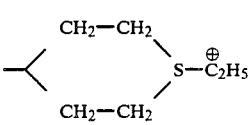
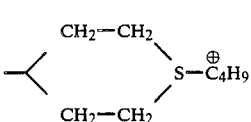
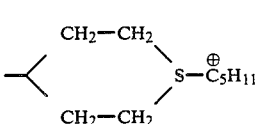
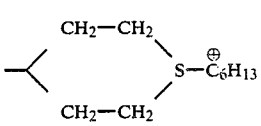
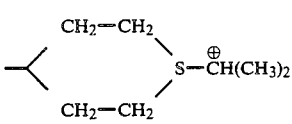
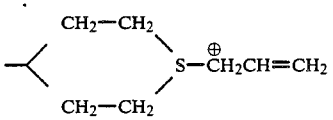
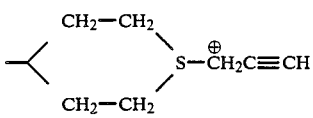
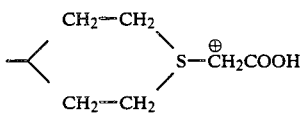
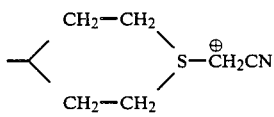

29
-continued
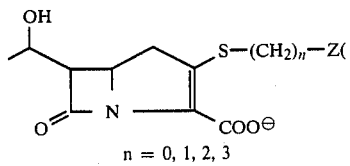
n = 0, 1, 2, 3
Z =
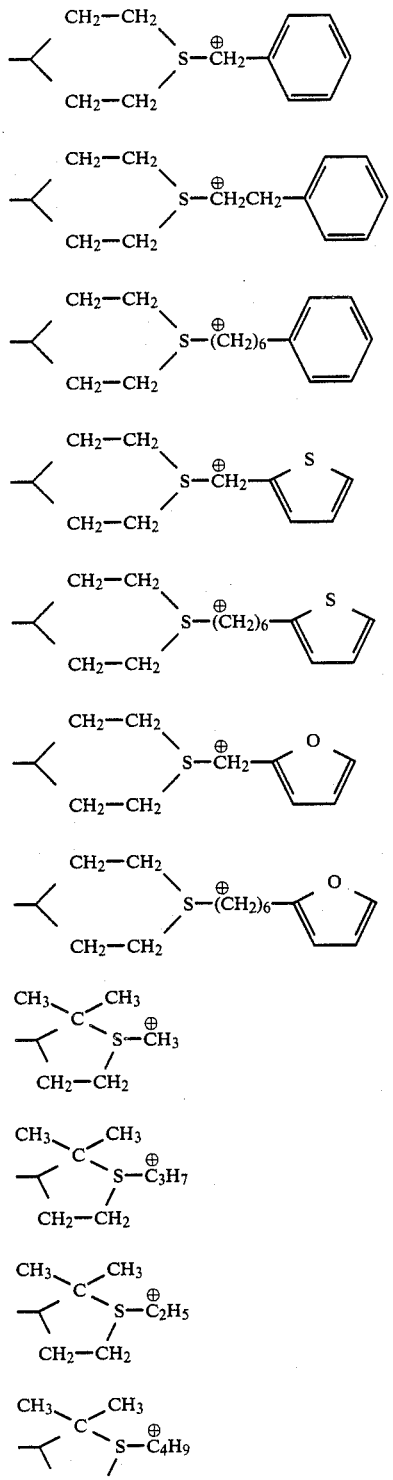
30
-continued
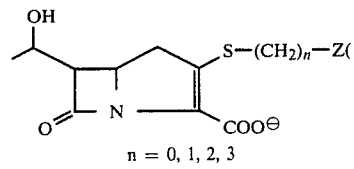
n = 0, 1, 2, 3
Z =
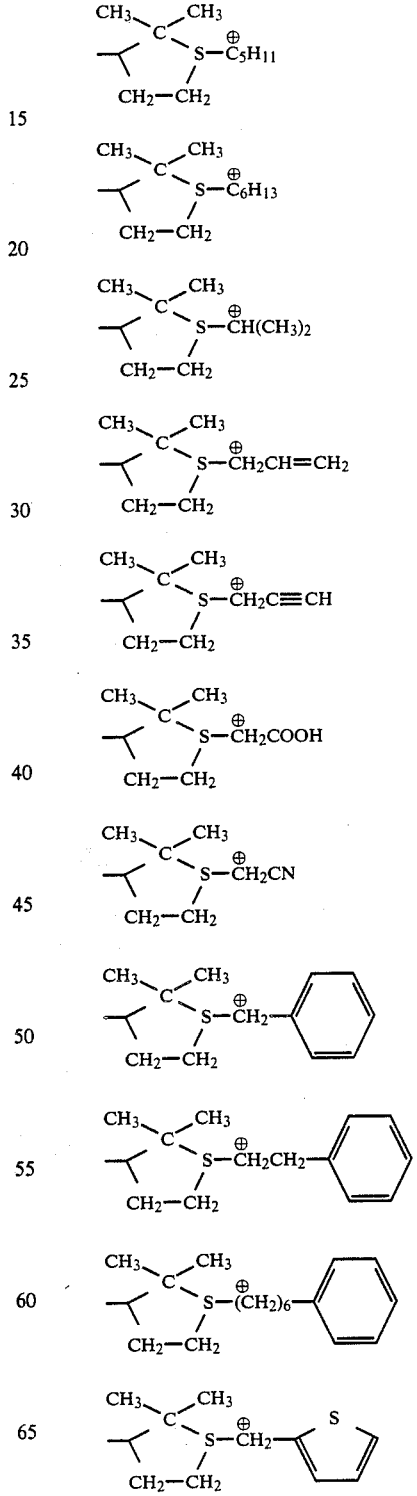

| 31 | 32 |
|---|---|
| 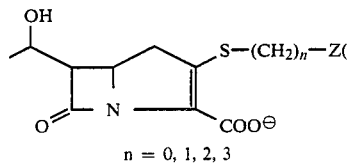 | 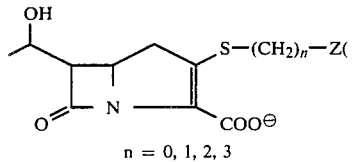 |
| n = 0, 1, 2, 3 | n = 0, 1, 2, 3 |

-continued
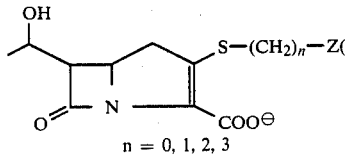
n = 0, 1, 2, 3
Z =
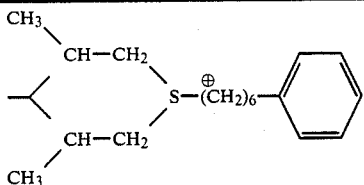
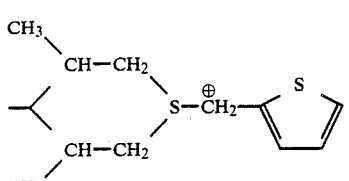
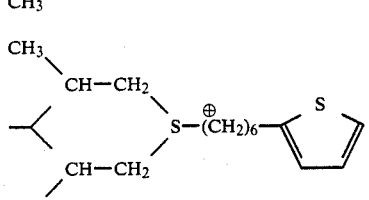
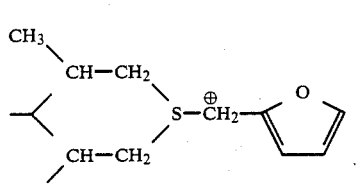
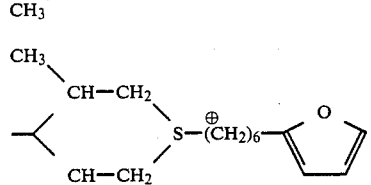
EXAMPLE 4
Following the general procedure of Example 2, the following compounds may be prepared by use of the appropriate starting materials.
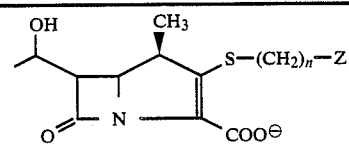
n = 0, 1, 2, 3
Z =
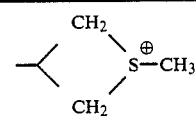
-continued
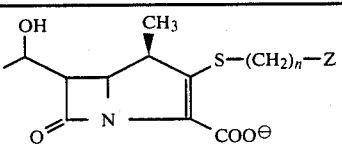
n = 0, 1, 2, 3
Z =
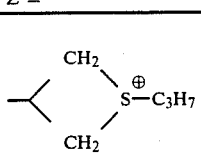
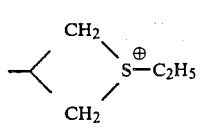
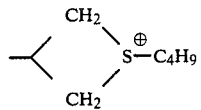
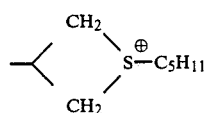
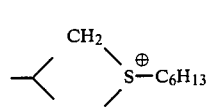
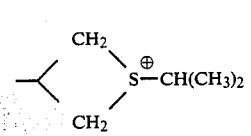
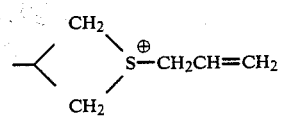
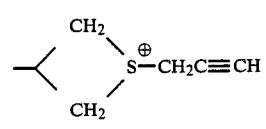
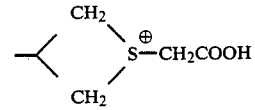
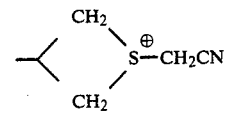
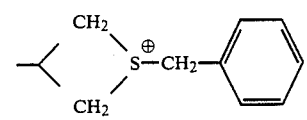

-continued
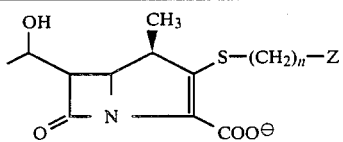
n = 0, 1, 2, 3
Z =
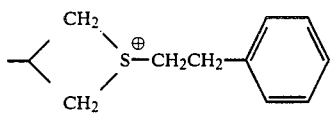
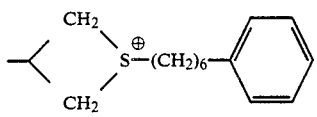
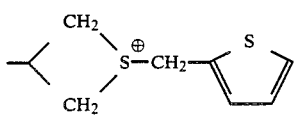
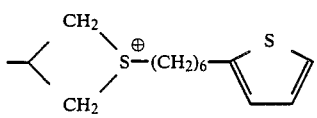
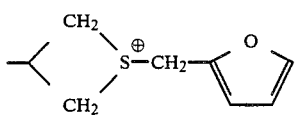
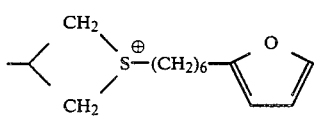
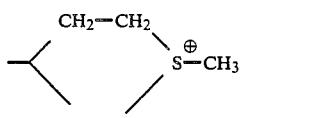
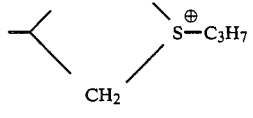
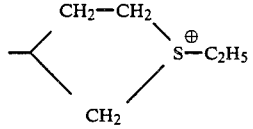
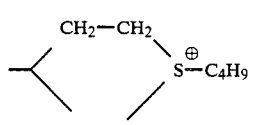
-continued
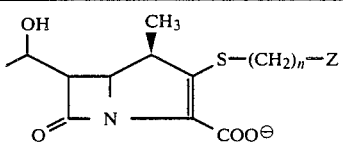
n = 0, 1, 2, 3
Z =
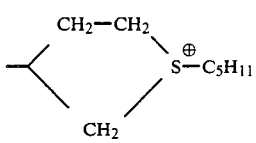
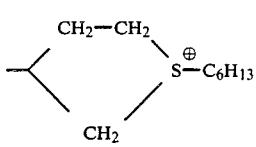
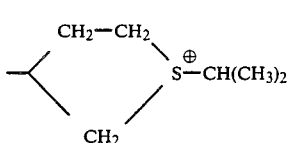
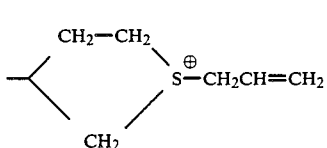
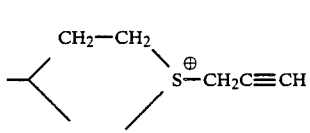
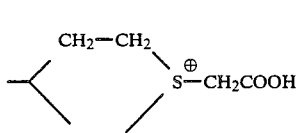
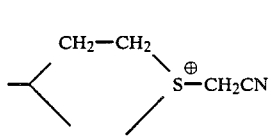
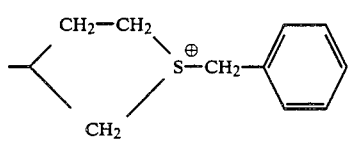

-continued
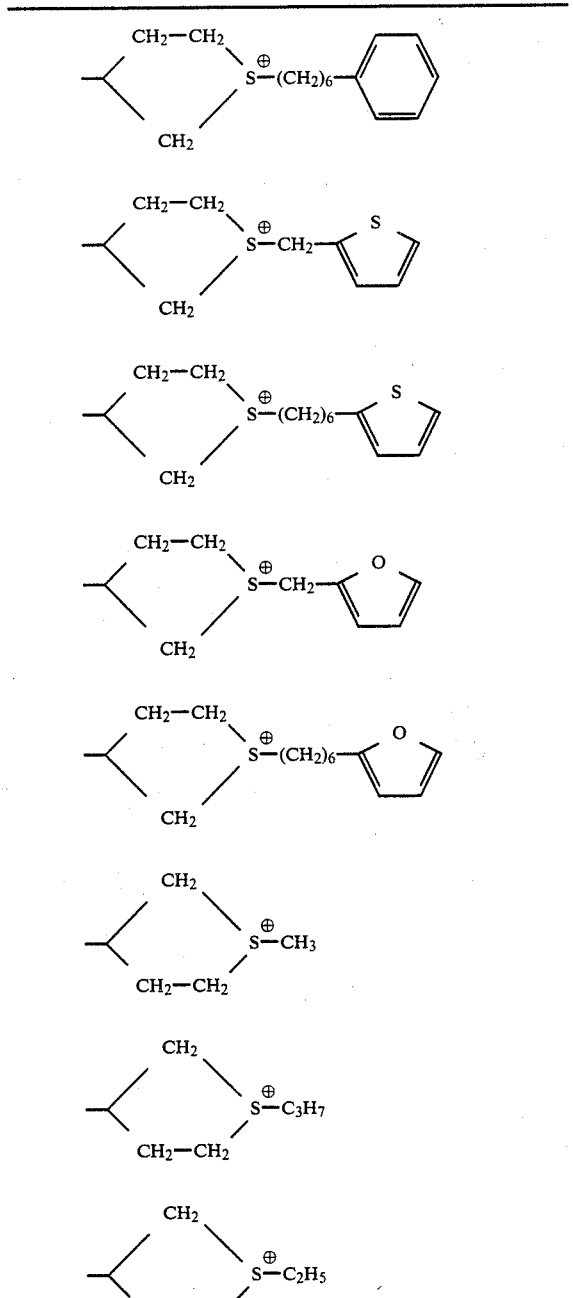
n = 0, 1, 2, 3
Z =
-continued
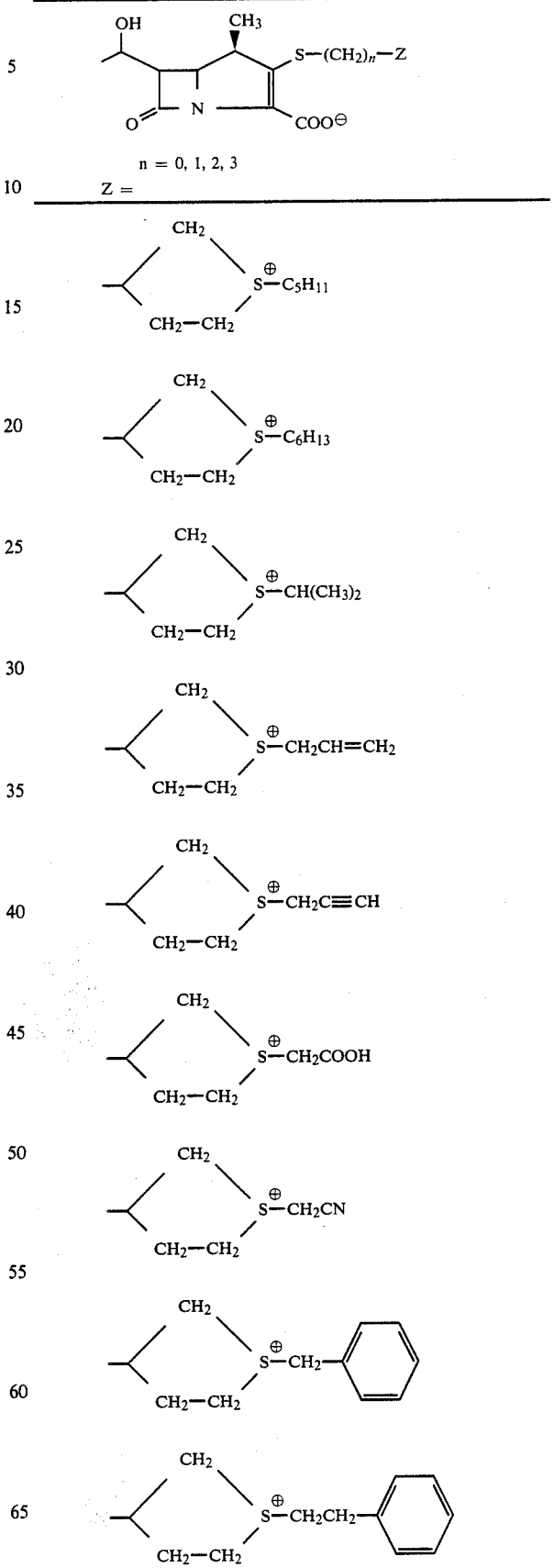
n = 0, 1, 2, 3
Z =

-continued
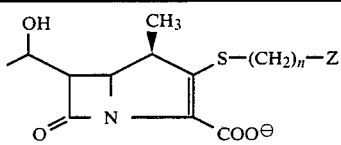
n = 0, 1, 2, 3
Z =
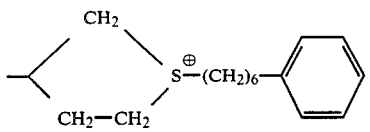
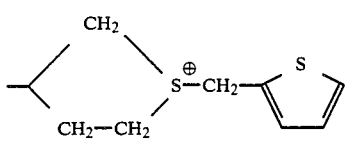
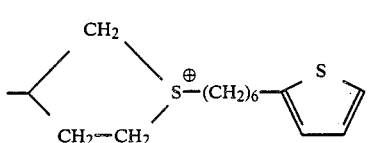
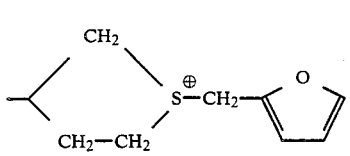
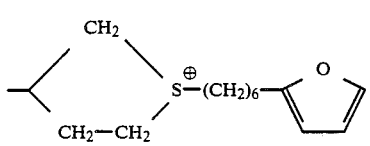
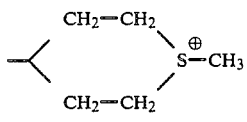
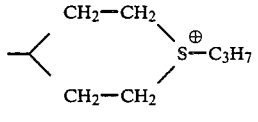
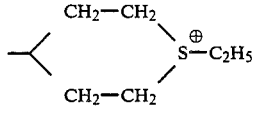
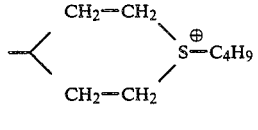
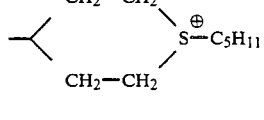
-continued
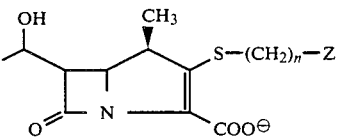
n = 0, 1, 2, 3
Z =
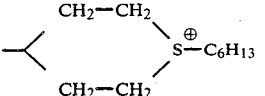
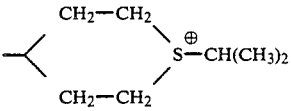
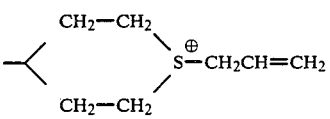
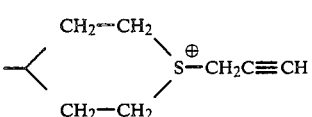
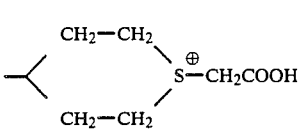
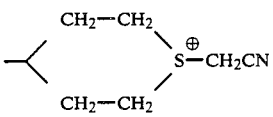
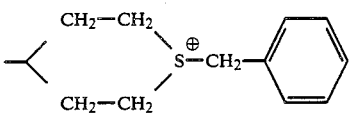
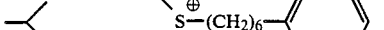
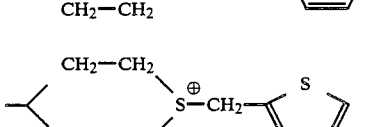
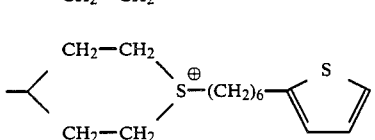

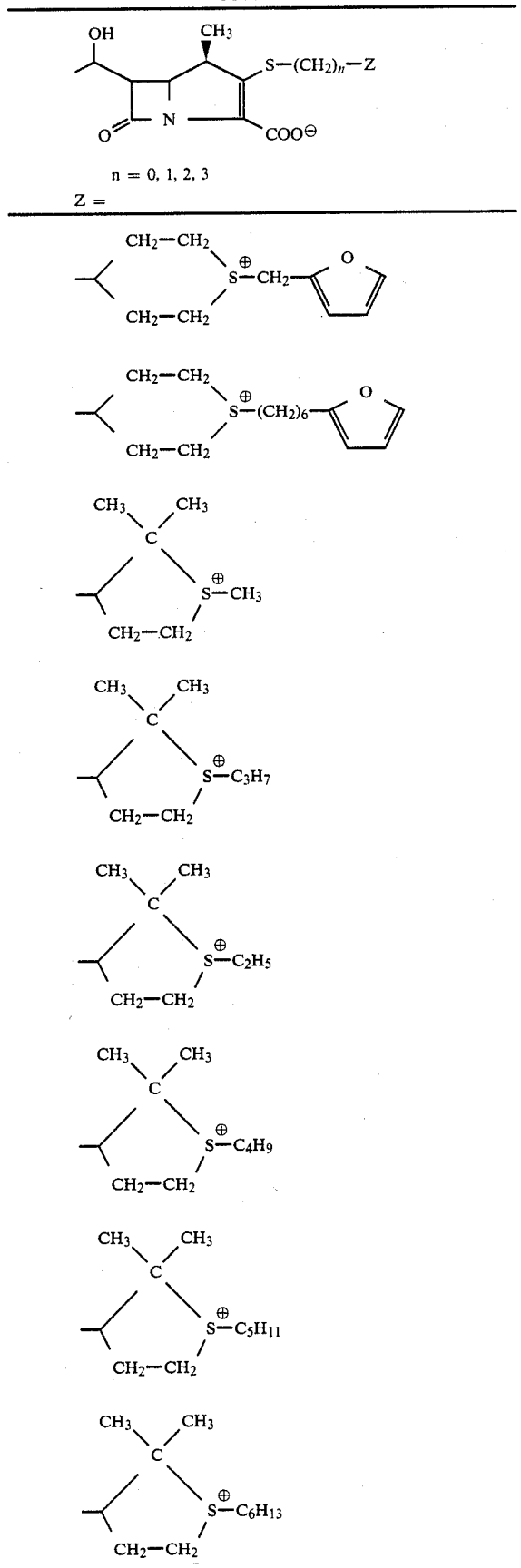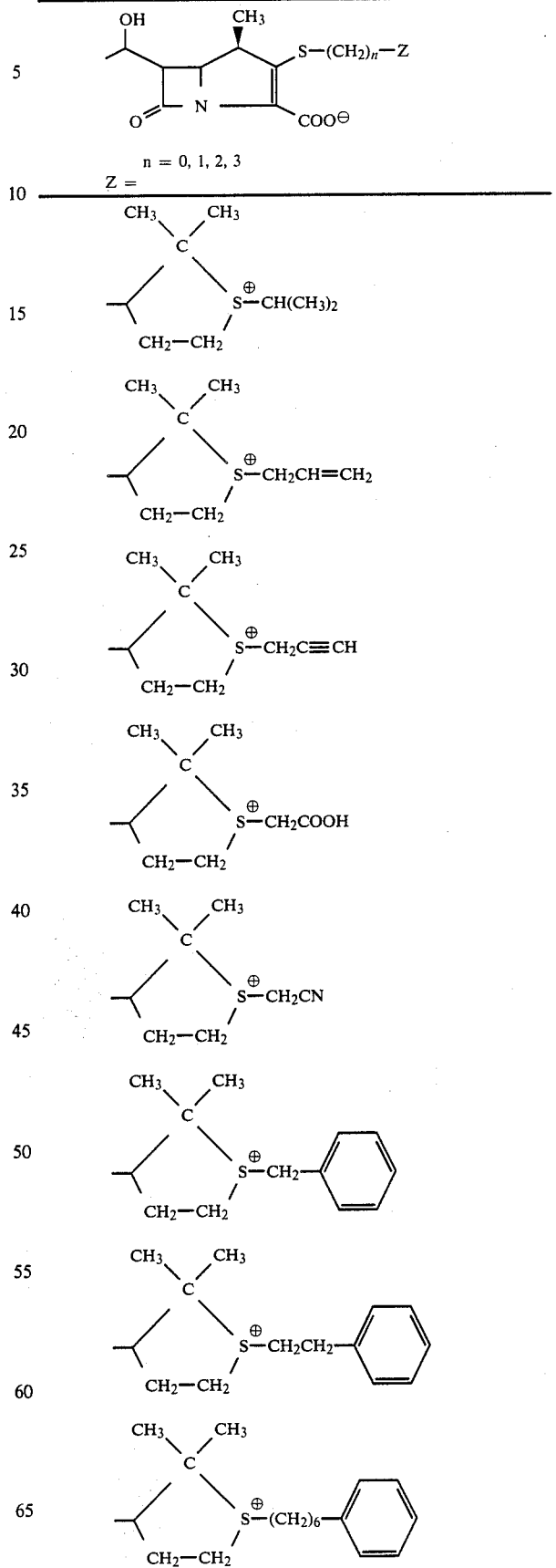

-continued
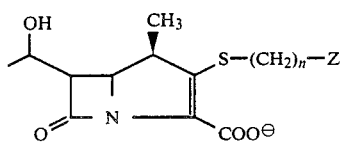
n = 0, 1, 2, 3
Z =
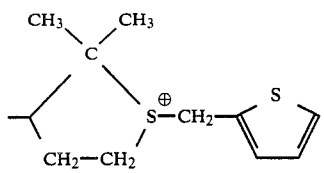
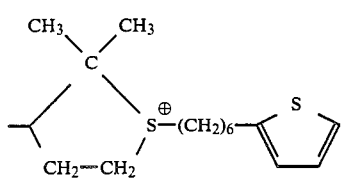
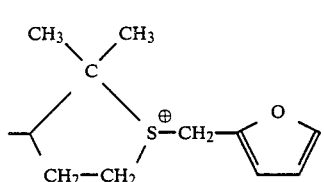
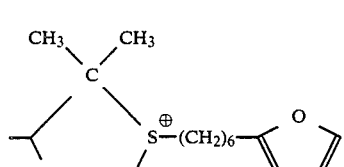
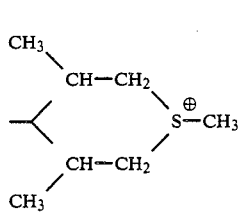
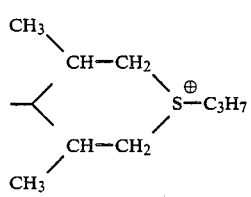
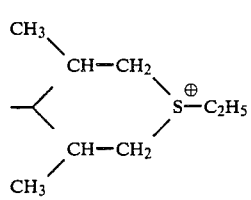
-continued
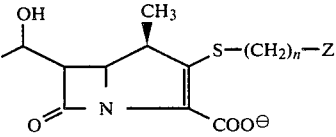
n = 0, 1, 2, 3
Z =
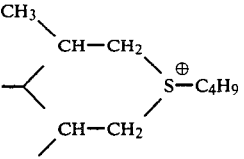
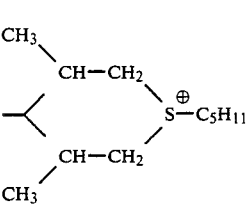
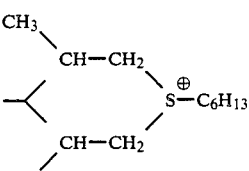
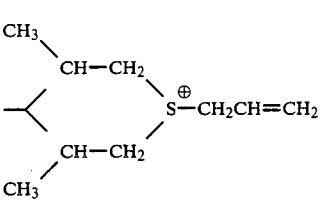
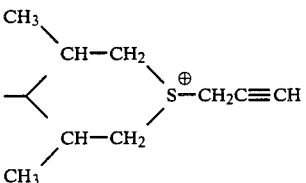
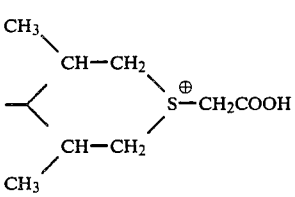
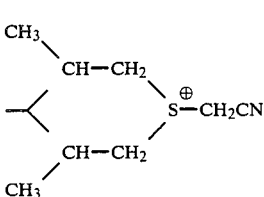

-continued

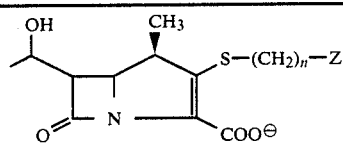

n = 0, 1, 2, 3
Z =

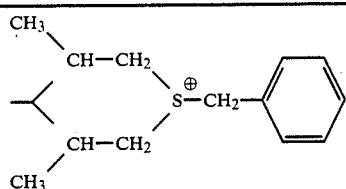

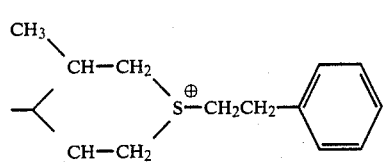

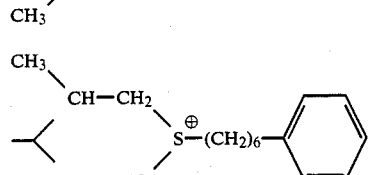

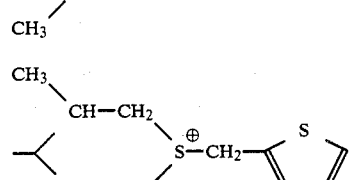

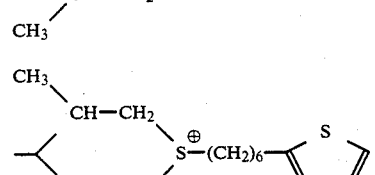

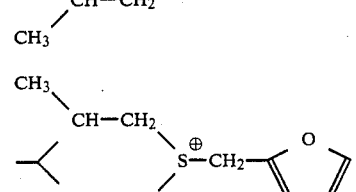

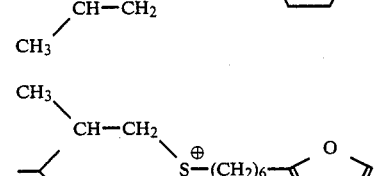

What is claimed is:
1. A compound having the formula

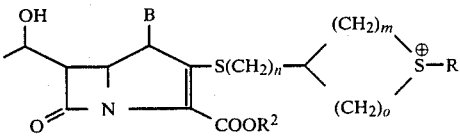

wherein $R^2$ is hydrogen or a conventional readily removable carboxyl protecting group, B is hydrogen or methyl, n is 0, 1, 2, or 3, m is 1 or 2, o is 1 or 2 and R is $C_1$-$C_6$ alkyl, allyl, propargyl carboxymethyl, cyanomethyl, or aralkyl in which the aryl moiety is phenyl or a 5-6 membered heteroaryl group selected from thienyl or furyl and the alkyl moiety is $C_1$-$C_6$ alkyl, said heterocyclic ring containing the sulfonium group being optionally substituted at a ring carbon atom or atoms by one or two $C_1$-$C_6$ alkyl groups, or a pharmaceutically acceptable salt or physiologically hydrolyzable ester thereof.

2. A compound of claim 1 wherein R is $C_1$-$C_6$ alkyl, or a pharmaceutically acceptable salt or physiologically hydrolyzable ester thereof.

3. A compound of claim 1 or claim 2 wherein B is hydrogen, or a pharmaceutically acceptable salt or physiologically hydrolyzable ester thereof.

4. A compound of claim 1 or claim 2 wherein B is methyl, or a pharmaceutically acceptable salt or physiologically hydrolyzable ester thereof.

5. A compound having the formula

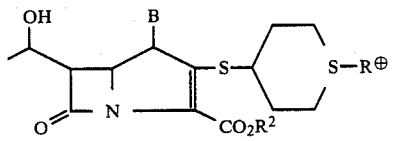

wherein $R^2$ is hydrogen or a conventional readily removable carboxyl protecting group, B is hydrogen or methyl, and R is $C_1$-$C_6$ alkyl, allyl, propargyl, carboxymethyl, cyanomethyl or aralkyl in which the aryl moiety is phenyl or a 5-6 membered heteroaryl group selected from thienyl or furyl and the alkyl moiety is $C_1$-$C_6$ alkyl, or a pharmaceutically acceptable salt or physiologically hydrolyzable ester thereof.

6. A compound of claim 5 wherein R is $C_1$-$C_6$ alkyl, or a pharmaceutically acceptable salt or physiologically hydrolyzable ester thereof.

7. A compound of claim 5 or claim 6 wherein B is hydrogen, or a pharmaceutically acceptable salt or physiologically hydrolyzable ester thereof.

8. A compound of claim 5 or claim 6 wherein B is methyl, or a pharmaceutically acceptable salt or physiologically hydrolyzable ester thereof.

9. A compound having the formula

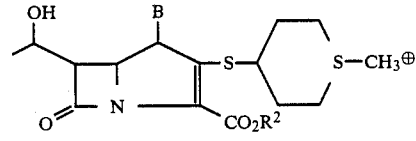

wherein $R^2$ is hydrogen or a conventional readily removable carboxyl protecting group and B is hydrogen or methyl or a pharmaceutically acceptable salt or physiologically hydrolyzable ester thereof.

10. A compound of claim 9 wherein B is hydrogen, or a pharmaceutically acceptable salt or physiologically hydrolyzable ester thereof.

11. A compound of claim 9 wherein B is methyl, or a pharmaceutically acceptable salt or physiologically hydrolyzable ester thereof.

12. A compound of claim 11 wherein B is β-methyl, or a pharmaceutically acceptable salt or physiologically hydrolyzable ester thereof.

13. The compound of claim 10 which is (5R,6S)-6-(1R-hydroxyethyl)-7-oxo-3-(1-methyl-4-thiatetrahydrothiopyranium)-1-azabicyclo[3.2.0]-hept-2ene-2-carboxylate.

14. The compound of claim 10 which is (5R, 6S)-6-(1R-hydroxyethyl)-4R-methyl-7-oxo-3-(1-methyl-4-thiatetrahydrothiopyranium)-1-azabicyclo[3.2.0]hept-2-ene-2-carboxylate.

* * * * *